(12) United States Patent
Wysocki et al.

(10) Patent No.: US 10,315,087 B2
(45) Date of Patent: *Jun. 11, 2019

(54) INTEGRATED MEDIA JUKEBOX AND PHYSIOLOGIC DATA HANDLING APPLICATION

(71) Applicant: Apple Inc., Cupertino, CA (US)

(72) Inventors: Christopher R. Wysocki, Los Gatos, CA (US); David Heller, San Jose, CA (US); Amandeep Jawa, San Francisco, CA (US); Sandeep Gupta, Fremont, CA (US); Greg Marriott, Honolulu, HI (US); Max Sprauer, San Jose, CA (US); David A. Shayer, Palo Alto, CA (US); John Wesley Archibald, Sunnyvale, CA (US); Shannon E. Wells, Santa Clara, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/871,775

(22) Filed: Jan. 15, 2018

(65) Prior Publication Data

US 2018/0133573 A1 May 17, 2018

Related U.S. Application Data

(60) Continuation of application No. 14/263,813, filed on Apr. 28, 2014, now Pat. No. 9,868,041, which is a
(Continued)

(51) Int. Cl.
*G06F 3/00* (2006.01)
*G06F 13/12* (2006.01)
(Continued)

(52) U.S. Cl.
CPC ...... *A63B 69/0028* (2013.01); *A63B 71/0686* (2013.01); *G06F 3/002* (2013.01);
(Continued)

(58) Field of Classification Search
CPC .... G06F 3/0601; G06F 9/4411; G06F 13/385; G06F 2003/0692; G06F 3/00;
(Continued)

(56) References Cited

U.S. PATENT DOCUMENTS

6,837,827 B1 * 1/2005 Lee .................. A63B 24/0084
482/3
2002/0022551 A1 * 2/2002 Watterson .............. A63B 22/02
482/8
(Continued)

*Primary Examiner* — Farley Abad
*Assistant Examiner* — Henry W Yu
(74) *Attorney, Agent, or Firm* — Fletcher Yoder PC (57) ABSTRACT

A method is provided to operate a computer to interoperate with a portable media player. The method includes processing signals provided from the portable media player to the computer that are indicative of whether an accessory has been connected to the portable media player, to determine whether the accessory has been connected to the portable media player. Based on a determination that the accessory has been connected to the portable media player, physiologic data of a user that was provided to the portable media player from a wireless physiologic data gathering device, is received from the portable media player, into the computer, via the accessory.

20 Claims, 9 Drawing Sheets

Related U.S. Application Data continuation of application No. 13/605,939, filed on Sep. 6, 2012, now abandoned, which is a division of application No. 11/419,737, filed on May 22, 2006, now abandoned.

(51) Int. Cl.

| | |
|---|---|
| *A63B 71/00* | (2006.01) |
| *G01H 7/00* | (2006.01) |
| *A61B 5/00* | (2006.01) |
| *A61B 6/04* | (2006.01) |
| *A63B 69/00* | (2006.01) |
| *G06F 16/438* | (2019.01) |
| *A63B 71/06* | (2006.01) |
| *G06Q 50/22* | (2018.01) |
| *G06F 17/30* | (2006.01) |
| *G06F 19/00* | (2018.01) |

(52) U.S. Cl.
CPC .... *G06F 16/4387* (2019.01); *G06F 17/30053* (2013.01); *G06F 19/00* (2013.01); *G06Q 50/22* (2013.01); *A63B 71/0622* (2013.01); *A63B 2071/0625* (2013.01); *A63B 2225/20* (2013.01); *A63B 2225/50* (2013.01)

(58) Field of Classification Search
CPC ............... G06F 17/30053; H04L 43/00; H04L 43/0817; A63B 69/0028; A63B 71/0686; A63B 71/0622
USPC .................. 710/2, 15, 18, 62, 64, 72; 482/8; 84/612, 615; 600/300, 519, 545; 707/102, 104.1
See application file for complete search history.

(56) References Cited

U.S. PATENT DOCUMENTS

| | | | |
|---|---|---|---|
| 2006/0028845 A1* | 2/2006 | Lin ...................... | G02B 6/0055 362/623 |
| 2006/0169125 A1* | 8/2006 | Ashkenazi ......... | A63B 71/0686 84/612 |
| 2007/0025194 A1* | 2/2007 | Morse .................. | G11B 27/034 369/30.1 |
| 2007/0113726 A1* | 5/2007 | Oliver .................. | A61B 5/0006 84/615 |
| 2007/0168388 A1* | 7/2007 | Plastina ............... | G11B 27/034 |
| 2007/0260483 A1* | 11/2007 | Nurmela ................ | A61B 5/222 705/2 |

\* cited by examiner

INTEGRATED MEDIA JUKEBOX AND PHYSIOLOGIC DATA HANDLING APPLICATION

RELATED APPLICATIONS

This is a continuation application of and claims priority to U.S. patent application Ser. No. 14/263,813 filed 28 Apr. 2014, which is a continuation application of and claims priority to, U.S. patent application Ser. No. 13/605,939, titled "Integrated Media Jukebox and Physiologic Data Handling Application," by the same inventors, which was filed on 6 Sep. 2012. The application is also a divisional application of and claims priority to now-abandoned U.S. patent application Ser. No. 11/419,737, titled "Integrated Media Jukebox and Physiologic Data Handling Application," by the same inventors, which was filed on 22 May 2006, to which parent application Ser. No. 13/605,939 also claims priority. These applications are incorporated by reference.

This application is related to U.S. patent application Ser. No. 11/566,072, filed 22 May 2006, and entitled "Activity: Monitoring System," which is hereby incorporated by reference herein. This application is also related to U.S. patent application Ser. No. 11/439,521, filed 22 May 2006, and entitled "Communication Protocol for Use with Portable Electronic Devices," which is hereby incorporated by reference herein.

BACKGROUND OF THE INVENTION

The use of devices to obtain exercise performance information is known. For example, simple mechanical pedometers have been used to obtain information relating to walking or running. A typical mechanical pedometer is a standalone device merely displays an indication of number of steps taken which, typically at most, can be converted to distance traveled by multiplying the number of steps taken by an estimated average stride size.

Recently, more sophisticated devices are known. For example, as described in U.S. Pat. No. 6,898,550 (the '550 patent), a foot-mounted unit, including a sensor for sensing motion of the foot of a user, is configured to provide motion information wirelessly—to a wrist-mounted unit. The wrist-mounted unit includes a display for displaying information to the user based upon data accumulated by the foot-mounted unit and transmitted wirelessly to the wrist-mounted unit. In addition, as described in the '550 patent, the wrist-mounted unit may be coupled to a computer and/or a network server via a network. The user can operate software running on the computer and or the server to analyze received data and/or to select operating parameters for the wrist-mounted unit and/or the foot-mounted unit.

The inventors have realized that a media jukebox computer application, including functionality to interact with a portable media player, may be synergistically combined with functionality to handle physiologic data from a physiologic data gathering device that is in communication with the portable media player for providing physiologic data to the portable media player.

SUMMARY

A method is provided to operate a computer to interoperate with a portable media player. The method includes processing signals provided from the portable media player to the computer that are indicative of whether an accessory has been connected to the portable media player, to determine whether the accessory has been connected to the portable media player. Based on a determination that the accessory has been connected to the portable media player, physiologic data of a user that was provided to the portable media player from a wireless physiologic data gathering device, is received from the portable media player, into the computer, via the accessory.

DETAILED DESCRIPTION

Figure 1:
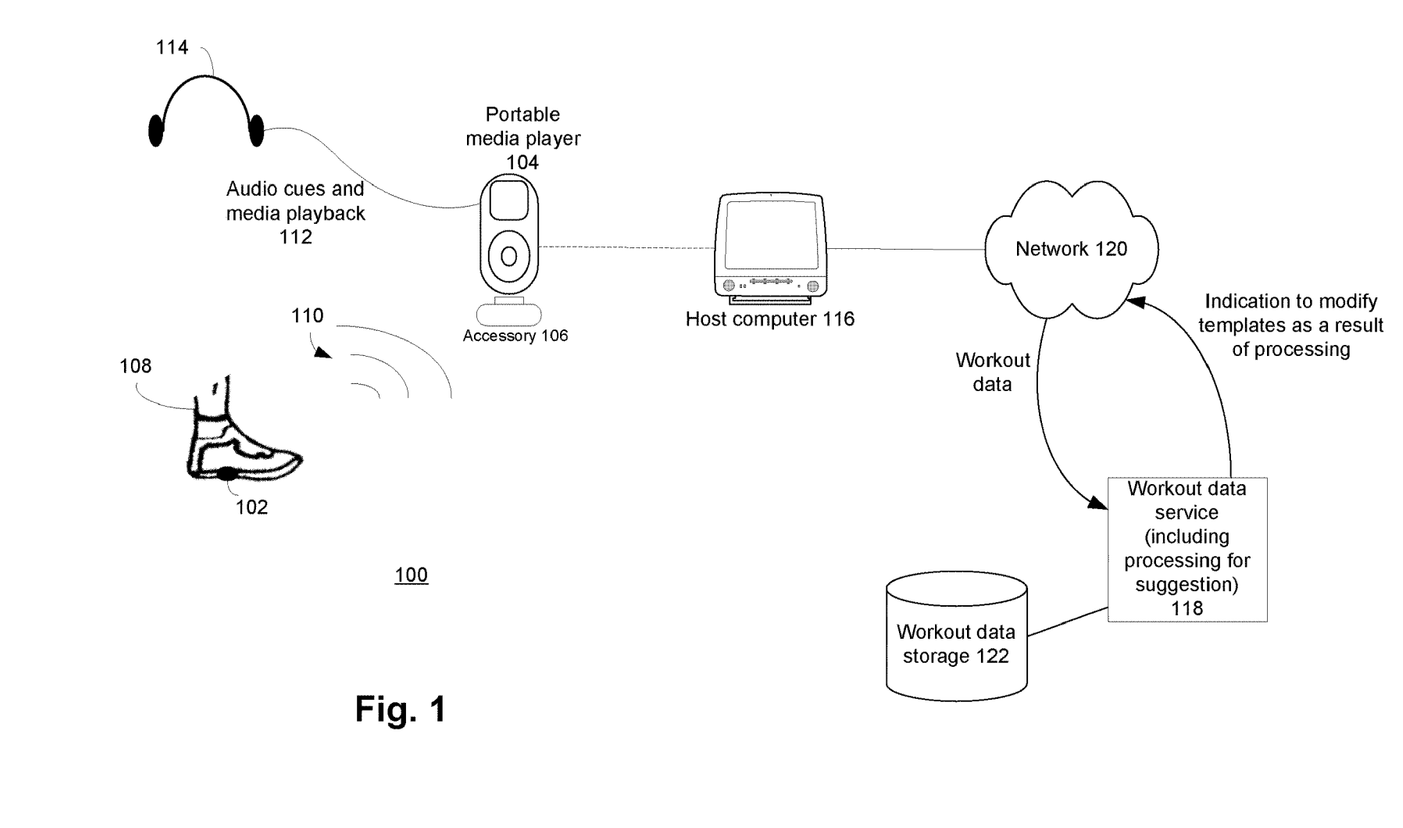
FIG. 1 illustrates an example of a system, including a portable media player, generally usable for, among other things, monitoring and/or controlling user exercise or other activity or physiology.

FIG. 1 illustrates an example of a system 100, including a portable media player 104, generally usable for, among other things, monitoring and/or controlling user exercise or other activity or physiology. Referring to FIG. 1, user exercise data is communicated (in this example, wirelessly) from a data gathering device 102, configured for gathering physiological data of a user (such as a sensor to sense the foot motion of a user), to the portable media player 104. In one example, the wireless communication is via an accessory 106, configured to selectively attach to a data port of the portable media player 104. An example of the accessory 106, and the interoperation of the accessory with the portable media player 104, is described in some detail in related U.S. patent application Ser. No. 11/439,521, filed 22 May 2006, and entitled "COMMUNICATION PROTOCOL FOR USE WITH PORTABLE ELECTRONIC DEVICES", referenced above, and incorporated by reference herein, in the section entitled "Cross Reference to Related Applications."

In operation, while a user 108 is exercising, physiological data of the user is accumulated by the data gathering device 102 and is provided wirelessly (via radio frequency waves 110, in one example) to the portable media player 104. Meanwhile, cues relative to the exercise (e.g., audio cues) as indicated by exercise templates, are being provided from the portable media player 104 to the user 108 (e.g., via a wire 112 and headphones 114). In addition to providing the cues relative to the exercise, the portable media player 104 may also be configured to provide playback of media (such as audio media) to the user 108 (e.g., like with the audio cues, via the wire 112 and headphones 114).

The playback of media may be coordinated with the exercise cues. For example, the playback of media may be using a playlist such as created using the iTunes® software application, provided by Apple Computer, Inc., running on a host computer 116 connectable to the portable media player 104. The playlists may be incorporated with, or corresponded to, the exercise templates on which the exercise cues are based.

Going in the direction from the portable media player 104 to the host computer 116, the portable media player 104 is configured to provide physiologic data to a workout data service 118, for storage 122, via the host computer 116 and a network 120 such as the internet. In some examples, the host computer 116 operates substantially as a conduit for providing the physiologic data to the workout data service 118 for storage 122. In other examples, the host computer 116 performs some processing on the physiologic data, temporarily stores the physiologic data for later forwarding (e.g., during a temporary loss of connection between the host computer 116 and the service 118 via the network 120), or both.

In yet other examples, not explicitly represented in FIG. 1, the physiological data is never or is only selectively provided to a service such as the workout data service 118. That is, the physiologic data may be maintained in storage on the portable media player 104, on the host computer 116, on both or on neither.

In still other examples, the physiological data is provided from the portable media player 104 to the workout data service 118 without being provided to a host computer such as the host computer 116. For example, the portable media player 104 may be incorporated into or, may be incorporated with, a telephone or other communication device that is connectable (e.g., wirelessly) to the workout data service 118.

With regard to the workout data service 118 and storage 122, in some examples, the physiologic data is processed at the workout data service 118. In one example, the physiologic data from one user is processed in view of physiologic data from other users to, for example, compare the users in terms of the physiologic data. In another example, the physiologic data is processed at the workout data service 118 to determine a suggested template change. For example, based on the processing at the workout data service 118, it may be suggested to change the clues to provide motivation at a particular portion of the workout. As another example, based on playlists associated with that workout by other users, a different playlist (or changes to the playlist) may be suggested for a particular workout.

Figure 2:
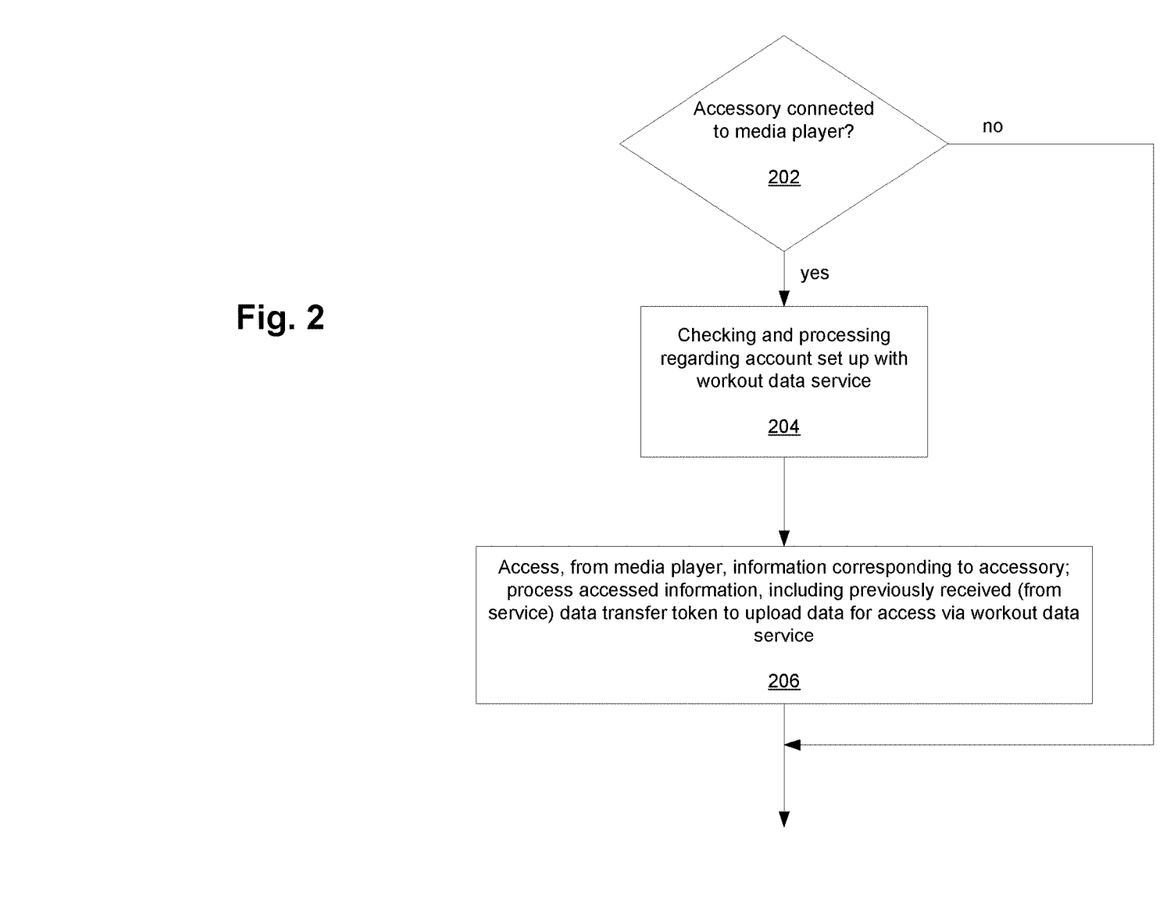
FIG. 2. is a flowchart illustrating an example of steps, mostly within a host computer, to accomplish transfer of physiologic data between a portable media player and a workout data service.

FIG. 2. is a flowchart 200 illustrating an example of steps, mostly within the host computer 116, to accomplish transfer of physiologic data between the portable media player 104 and the workout data service 118. At step 202, it is determined whether the accessory 106 has been connected to the portable media player 104, which would allow the physiological data to be received by the portable media player from the data gathering device 102.

The determination of whether the accessory 106 has been connected is, in one example, via configuration data that is provided to the host computer 116 when the portable media player 104 and the host computer 116 are connected, in a portion of a handshake protocol in which the portable media player 104 provides information to the host computer 116 regarding characteristics, capabilities and/or activities of the portable media player 104. In other examples, the accessory 106 is one of a plurality of possible accessories, and the check for the accessory 106 is merely part of a check for accessories generally. In yet other examples, mentioned below, processing like that in step 202 is not carried out at all.

If it is determined at step 202 that the accessory 106 has not been connected to the portable media player 104, then the FIG. 2 processing ends. Otherwise, if it is determined at step 202 that the accessory 106 has been connected to the portable media player 104, or if step 202 is not performed at all, then processing continues at step 204, to match the portable media player 104 to an account of the workout data service 118. At step 204, a check is made for an account for the user at the workout data service 118. If it is determined at step 204 that the user does not have an account at the workout data service 118, then the step 204 processing includes causing interaction with the user to set up an account at the workout data service 118. At step 206, the host computer accesses the physiologic data, if any, stored in the portable media player 104 (e.g., from a preset location of storage within the portable media player 104) and provides the physiologic data to the workout data service 118 to be associated with the user's account. In some examples, if a connection to the workout data service 118 is not available (e.g., there is no connection between the host computer 116 and the network), then step 206 is prevented from being performed.

The physiologic data may be provided from the portable media player 104 to the host computer 116, and further to the workout data service 118, in an XML-formatted file. In some examples, a portion of the provided data is retained on the portable media player 104, for easy reference by the user (e.g., during or in preparation for a workout). Communication between the host computer 116 and the workout data service 118 is typically via Secure Socket Layer, using the HTTPS protocol. In one example, a portion of the physiologic data is retained in storage of the portable media player 104 (e.g., the last "n" workouts) and can be displayed via a user interface of the portable media player 104. Furthermore, while the physiologic data is passed on to the workout data service 118 from the host computer 116, the host computer 116 may retain some or all of the physiologic data to, for example, display the data via a physiologic data user interface of a music store application operating on the host computer 116. An example user interface display of the music store application operation on the host computer 116, including a display of physiologic data, is described later, with reference to FIG. 8.

Figure 3:
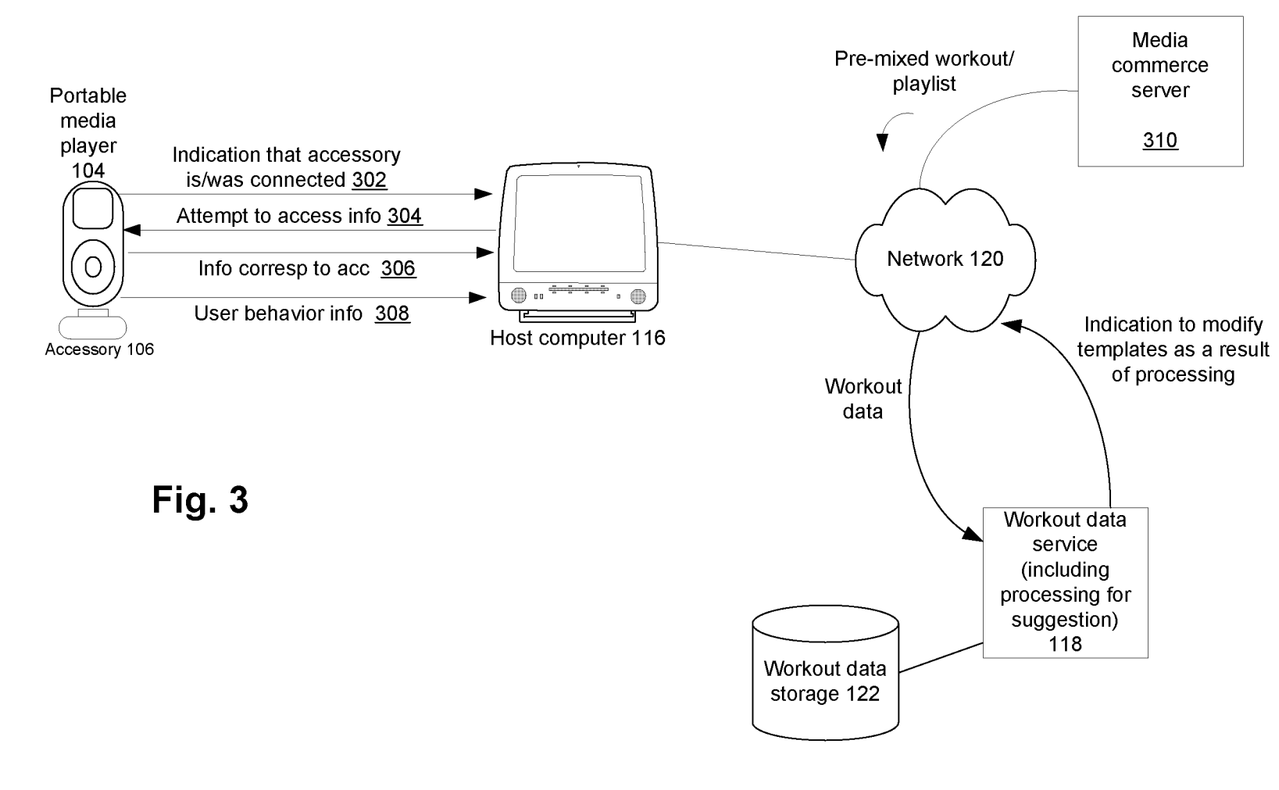
FIG. 3 is a schematic diagram that, while similar to FIG. 1, illustrates details of example configuration and operation of particular portions of the FIG. 1 system.

FIG. 3 is a schematic diagram that, while similar to FIG. 1, illustrates details of example configuration and operation of particular portions of the FIG. 1 system. As shown in FIG. 3, there are a number of signals involved in interoperation of the portable media player 104 and the host computer 116. A signal 302 is provided from the portable media player 104 indicating that the accessory 106, via which the data gathering device 102 (FIG. 1) communicates with the portable media player 104 is or was attached to the portable media player 104. The signal 304 represents an attempt by the host computer 116, in response, to access information on the portable media player 104 corresponding to the accessory 106 (i.e., physiologic data provided to the portable media player 104 from the data gathering device 102 via the accessory 106). The signal 306 represents the information corresponding to the accessory being provided from the portable media player 104 to the host computer 116.

In addition, the signal 308 represents feedback of user behavior information relative to the playback of media (which may also correspond to use/operation of the device 102 that provides physiologic data via the accessory 106) and, concomitantly, relative to the exercise cues. This feedback user behavior information signal 308 may be 8 used to modify (or suggest modifications to) the play lists, templates, or some combination thereof, based on the user's behavior as indicated by the signal 308. The modifications and/or suggested modifications may be a result of processing within the host computer 116 or, as discussed above, the modifications and/or suggested modifications may be a result of processing within the workout data service 118 (typically resulting from processing of physiologic data from the particular user and related data from a community of users, and not just from processing of physiologic data and related data from the particular user alone).

It is noted that, as alluded to above, while FIGS. 2 and 3 illustrate detecting whether the accessory 106 is or was connected to the portable media player 104, there are other examples in which the host computer 116 and the portable media player 104 interoperate such that the host computer 116 can determine whether there may be physiologic data, from the data gathering device 102, present on the portable media player to be provided to the host computer 116. For example, the host computer 116 may initiate a check in a predetermined area of the portable media player 104 storage (e.g., in a particular directory) for physiologic data for retrieval.

As also shown in FIG. 3, the host computer 116 may communicate with a media commerce service 310, via the network 120, to accomplish the purchase of exercise templates, which may also be combined with or otherwise indicate associated playlists. In this way, prepackaged workout/song mixes may be purchased. While the templates and playlists are typically purchased, there are circumstances in which the templates and playlists may be provided without cost (e.g., promotions).

Figure 4:
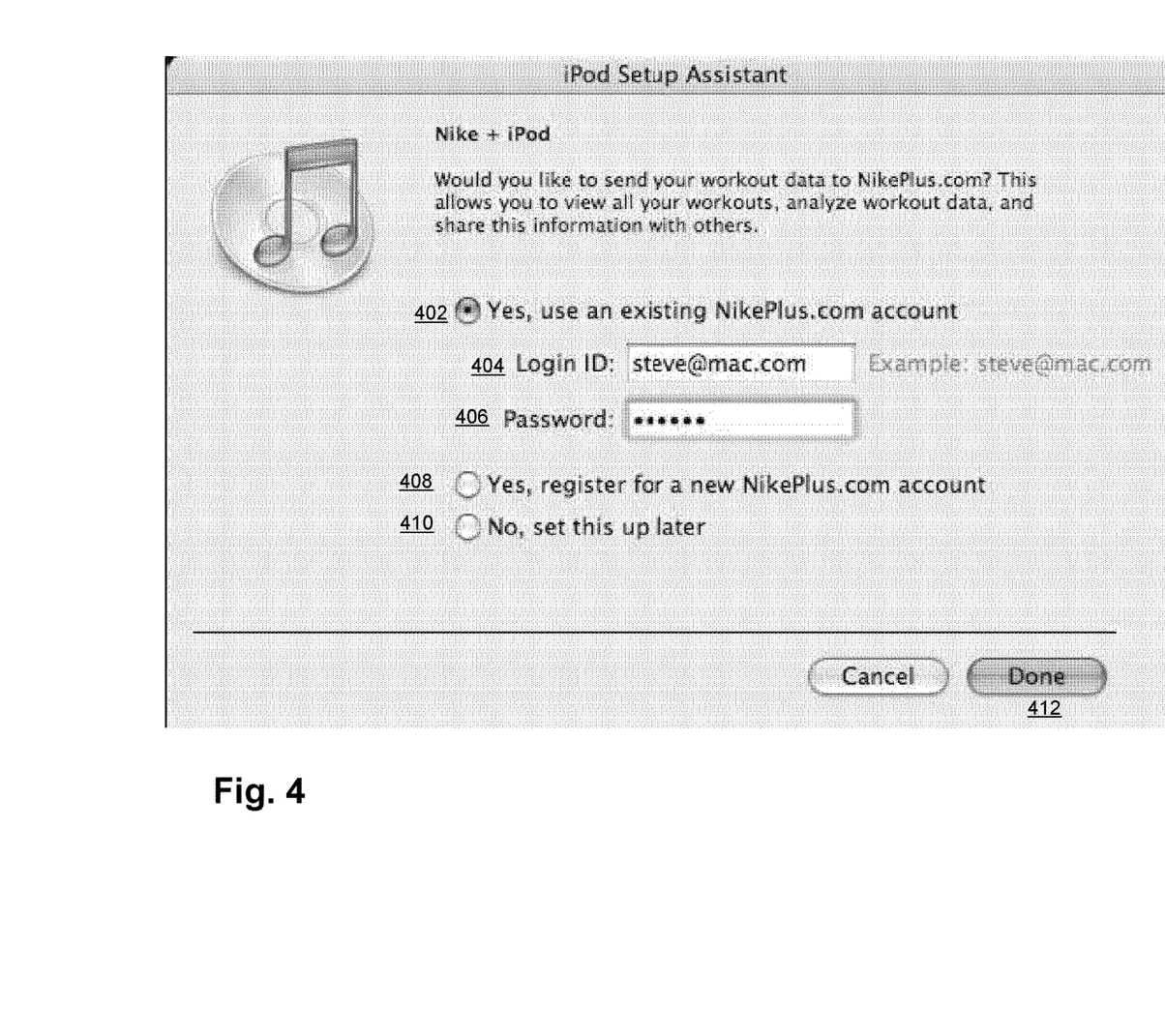
FIG. 4 is a screenshot that illustrates an example of a user interface of an application (such as a media jukebox application) on a host computer that may be provided to accomplish an account matching between a portable media player and a workout data service.

FIG. 4 is a screenshot that illustrates an example of a user interface of an application on the host computer 116 that may be provided to accomplish the account matching (step 204, in FIG. 2) between the portable media player 104 and the workout data service 118. The application may be, for example, a media jukebox application such as the iTunes® application, as discussed above. Referring to FIG. 4, an application in the host computer 116 displays a setup screen 400 to accomplish associating the physiologic data corresponding to a particular user with an account for that user at the workout data service 118. As can be seen from the FIG. 4 screenshot 400, if the user has a preexisting account with the workout data service 118, the user selects the radio button 402, and provides a login ID 404 and password 406 associated with the preexisting account. To register for a new account, the user selects the radio button 408, which (after selecting the "Done" button 412), causes presentation of an account creation page of the workout data service 118. The user indicates the account credentials (such as username and password) so that the physiologic data may be passed from the host computer 116 to an account at the workout data service 118 associated with the user. As also illustrated in FIG. 4, an option (radio button 410) is also provided to postpone the account access setup.

Once an account is matched between the portable media player 104 and the workout data service 118 for physiologic data received by the portable media player 104 via the accessory 106, account access credentials may be saved at the host computer 116 for later use. The account access credentials may even be saved at the portable media player 104 (to, for example, be subsequently provided to the host computer 116 along with physiologic data). In one example, account access credentials such as login ID and password are not themselves saved on either the host computer 116 or the portable media player 104. Rather, the workout data service 118 provides back to the host computer 116 an account access "token" that uniquely corresponds to the account access credentials and that provides only limited access to the workout data service 118, for providing physiologic data to the workout data service 118. For example, the full account access credentials may provide access to workout data service 118 functions such as ecommerce or other security-sensitive functions, for which it may be considered undesirable to store access credentials on the host computer 116 or on the portable media player 104.

Figure 5:
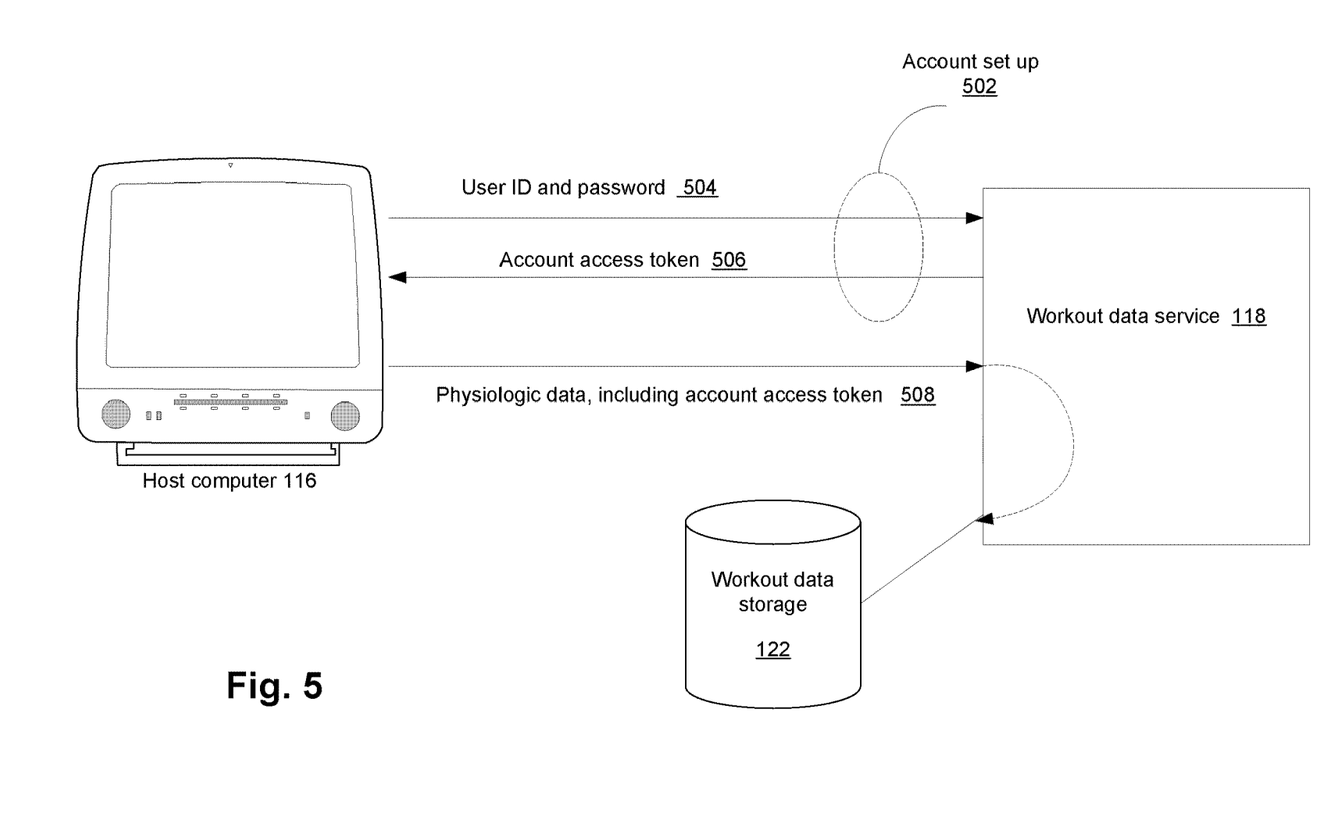
FIG. 5 schematically illustrates an example of signals involved in an interaction between a host computer and a workout data service with regard to account setup (FIG. 4) and use of an account access token.

FIG. 5 schematically illustrates an example of signals involved in the interaction between the host computer 116 and the workout data service 118 with regard to account setup (FIG. 4) and use of an account access token. The dashed oval 502 represents a portion of the account set up interaction between the host computer 116 and the workout data service 118. Specifically, arrow 504 represents account credentials (such as user ID and password) being provided from the host computer 116 to the workout data service 10 118. An account access token, corresponding to the account credentials) is provided back to the host computer 116 from the workout data service 118. In operation, to provide physiologic data to the workout data service 118 for storage 122, the account access token is provided to the workout data service 118 in conjunction with the physiologic data 508. As mentioned above, the workout data service 118 uses the account access token to grant limited access to the workout data service 118, for example, for storing the physiologic data and for associated analysis and/or viewing functions.

Figure 6A:
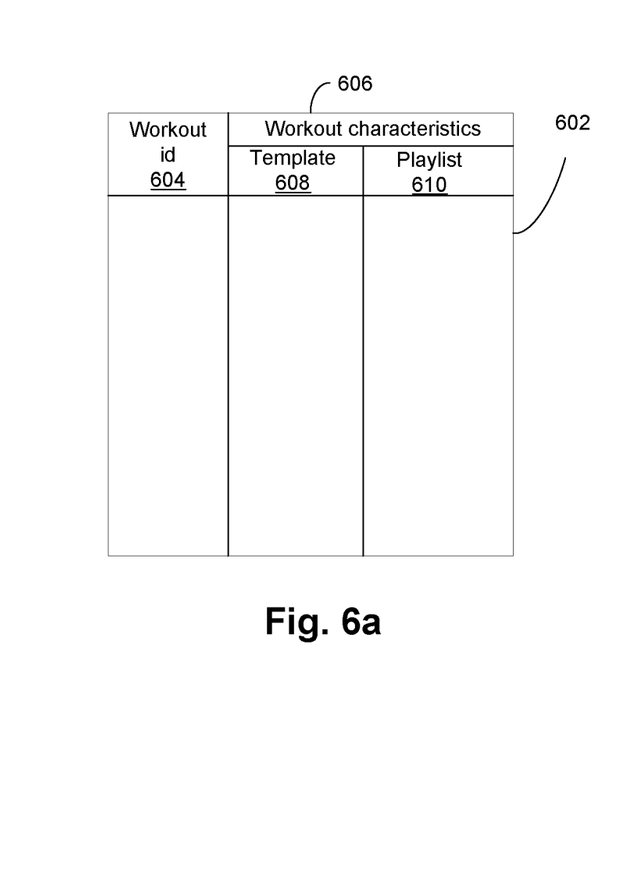
FIGS. 6a and 6b illustrate, in accordance with some examples, data structures that may be maintained within a portable media player, usable to correlate measurement and/or control of physical activity with playback of media.
Figure 6B:
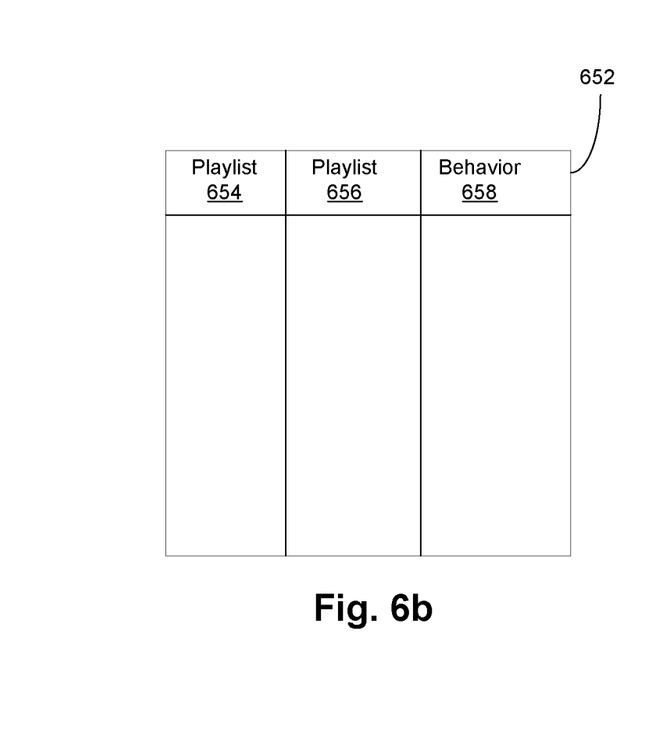

FIGS. 6a and 6b illustrate, in accordance with some examples, data structures that may be maintained within the portable media player 104, usable to correlate measurement and/or control of physical activity with playback of media. For example, the data structures may include a table 602 and a table 652. Each row of the table 602 is indexed by a workout id, in column 604. A workout id refers to a particular distinguishable workout, as now discussed. For example, for a particular workout (identified by a workout id), the column 606 (in one example, including two columns 608 and 610, as discussed shortly) includes an indication of workout characteristics.

In the FIG. 6a example, the workout characteristics in column 606 include a template designation 608 and a playlist designation 610. As discussed above, a template indicates cues, such as audio cues, corresponding to a particular workout. The playlist designation 610 indicates a play list, defining media playback associated with the workout.

FIG. 6b includes a table 652 of playlists maintained in the portable media player 104. The column 654 includes the playlist designation for each playlist. The column 656 indicates the media (typically, songs) corresponding to each playlist. The column 658 includes an indication of the user's behavior relative to the playlist. For example, the column 658 may indicate a workout id, that indicates a workout during which the user played the songs of the playlist (or, songs generally, even if not part of a playlist). As another example, the column 658 may includes an indication of user behavior to override the playlist, such as behavior to cause songs to be skipped. Referring back to FIG. 3, this user behavior information may be provided to the host computer 116 such that processing within the host computer 116 modifies play lists, forms play lists, associates playlists with workouts, or other results as appropriate, based on the user behavior information.

Figure 7:
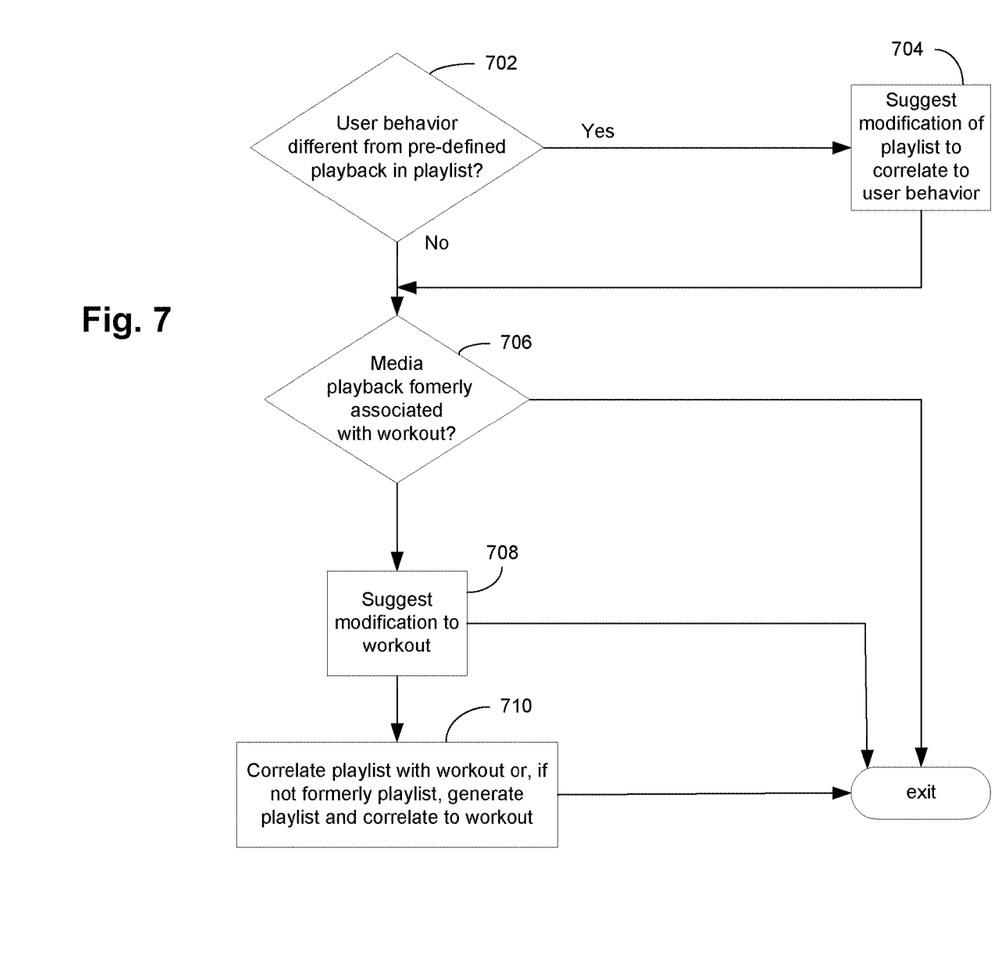
FIG. 7 is a flowchart illustrating an example of processing within a host computer to process user behavior information and other data in the FIG. 6 data structures.

FIG. 7 is a flowchart illustrating an example of processing within the host computer 116 to process the user behavior information and other data in the FIG. 6 data structures. At step 702, it is determined if the actual user behavior is different from the pre-defined playback behavior indicated by the corresponding playlist. For example, if the user behavior information indicates that the user overrode the playlist by skipping songs, then processing within the host computer 116, at step 704, suggests to the user, via a user interface, to allow playlist to be modified to correlate to the user behavior.

In some examples, the user behavior information may not be clearly indicative of a definite suggestion at step 704. For example, the user may have skipped one song each of ten times of processing the play list, whereas the user may have skipped a second song only one time of processing the play list. The suggestions may provide gradations of suggestion. For example, it may be strongly suggested to delete the first song (the one skipped ten times) from the playlist, whereas it may be mildly suggested to delete the second song (the one skipped only one time) from the playlist.

In the next steps shown in the FIG. 7 flowchart, processing is carried out to suggest associating a play list with a particular workout, based on the media playback as controlled manually by the user, during the particular workout. At step 706, it is determined from the user behavior information if the media playback during a workout (i.e., during processing of a particular workout template by the portable media player 104) corresponds to a pre-existing playlist. If so, then processing of FIG. 7 exits. If it is determined at step 706 that the media playback during the workout does not correspond to a pre-existing playlist then, at step 708, a correlation to the workout (i.e., to the template) is suggested. If the user agrees then, at step 710, the media playback is associated with a play list, and that playlist is associated with the workout.

Figure 8:
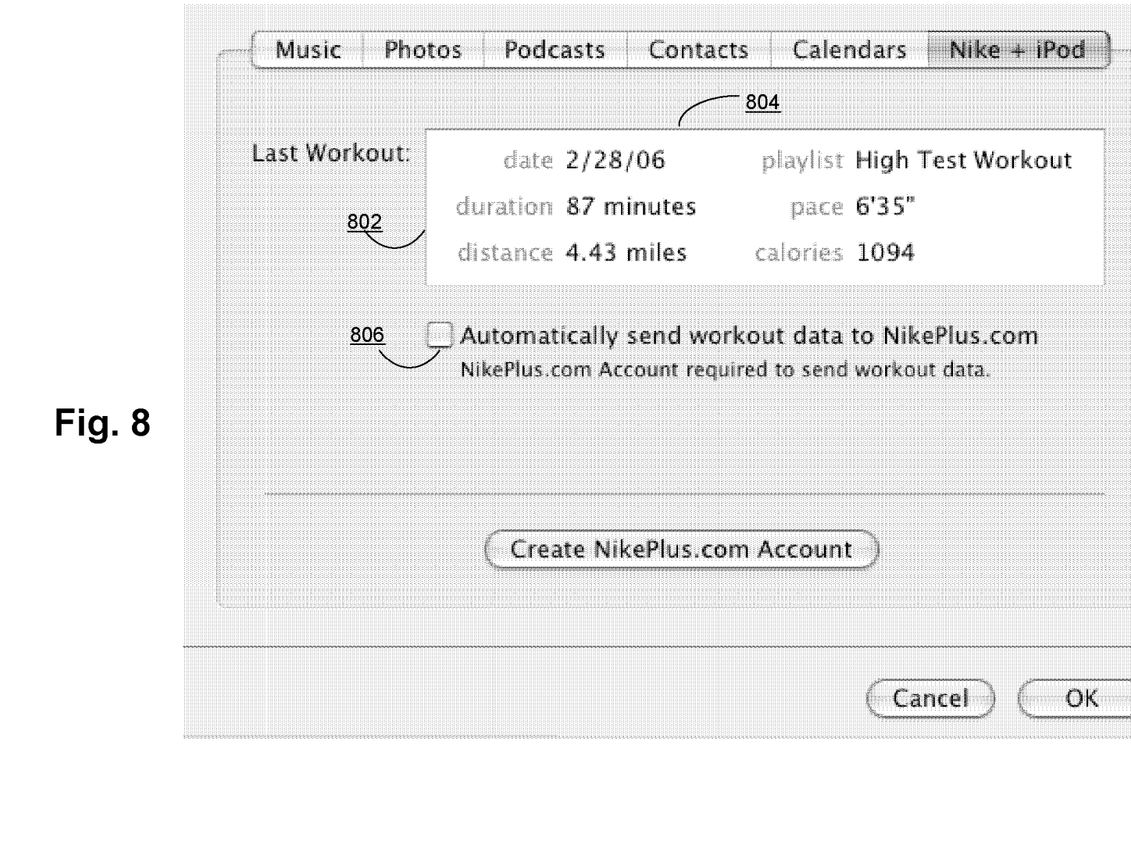
FIG. 8 illustrates a user interface screen, caused to be presented by processing within the host computer, to display an indication of some physiologic data.

As mentioned above, in some examples, physiologic data provided from a portable media player (such as the portable media player 104) to a workout data service (such as the workout data service 118) may be provided through a host computer (such as the host computer 116). FIG. 8 illustrates a user interface screen, caused to be presented by processing within the host computer, to display an indication of some of the physiologic data, namely, the physiologic information of the "last workout" in a portion 802 of the user interface screen. (This is just an example. An indication of other of the physiologic data may be displayed.) In addition to the information such as date, distance, pace and calories, the "last workout" information includes an indication 804 of the media play list associated with that workout. It is also of note that processing within the host computer 116 may also operate to automatically send the physiologic data to the workout data service 118 (e.g., accompanied by the access token discussed above, relative to FIG. S and the discussion of account set up with the workout data service 118), without ongoing user intervention. The user may control whether this automatic operation takes place via the check box 806 in the FIG. 8 user interface screen. This check box 806 would be initially unchecked if the user previously chose for physiologic data not to be sent at all to the workout data service 118, e.g. during initial setup (FIG. 4).

Figure 9:
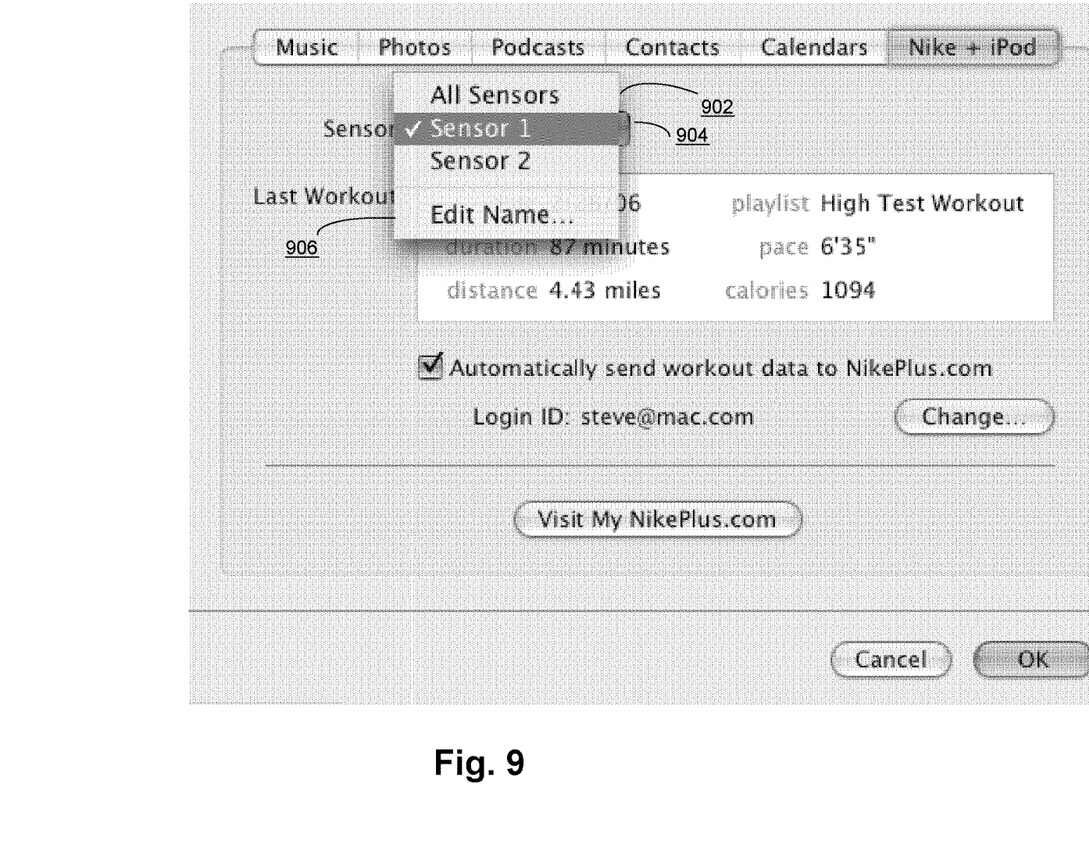
FIG. 9 illustrates a user interface screen, caused to be presented by processing within the host computer, to allow a user to choose between physiologic data gathering devices with which the portable media player has been paired.

While much of the previous description has described methods, applications and systems in the context of a single physiologic data gathering device, it has been mentioned above that there may be more than one physiologic data gathering device. FIG. 9 illustrates a user interface screen, caused to be presented by processing within the host computer, to allow a user to choose between physiologic data gathering devices with which the portable media player has been paired.

A menu item 902, in this case a pull down menu item, is provided to allow the user to choose which physiologic data gathering devices (listed as "sensors") for which data is to be considered and/or otherwise handled from within the application executing in the host computer. In FIG. 9, the "Sensor I" item 904 is checked. In addition, a user interface item 906 is provided to allow the user to edit the name ascribed to a particular physiologic data gathering device, relative to the application executing in the host computer.

In summary, then, we have described an overall architecture of a system, including a portable media player, generally usable for, among other things, monitoring and/or controlling user exercise or other activity or physiology. In addition, we have described how an application of a host computer, such as a media store application, operates in the context of such a system.

What is claimed:

1. A method, comprising:
   in a host computer, performing operations for:
   storing a workout playlist of songs for a workout template, the workout template comprising audio cues for a corresponding workout;
   processing the workout template, including playing songs in the workout playlist and playing the audio cues during the playing of the songs; and
   based on physiologic data indicative of user behavior, modifying the audio cues played during the playing of the songs.

2. The method of claim 1, comprising generating and storing a modified playlist as the workout playlist, based upon the physiologic data;
   wherein the generating and storing the modified playlist comprises:
   updating a corresponding entry in a workout identification table, the entry comprising a workout identification ("ID") and a play list ID, wherein the workout ID indicates workout characteristics for a workout corresponding to the workout ID and the playlist ID indicates a playlist that defines media playback associated with the workout;
   wherein the updating comprises updating the playlist ID with an identifier for the modified playlist.

3. The method of claim 2, wherein the entry in the workout identification table further comprises a template ID, the template ID indicating the audio cues for the corresponding workout.

4. The method of claim 1, comprising generating and storing a modified playlist as the workout playlist, based upon the physiologic data;
   wherein the generating and storing the modified playlist comprises:

updating a corresponding entry in a play list identification table with information about the modified playlist, the entry comprising a playlist ID and a listing of media in the workout playlist, wherein the playlist ID indicates a designation for the workout playlist;

wherein the updating comprises updating the playlist ID with an identifier for the modified playlist and updating the listing of media in the workout playlist to include media corresponding to the user behavior with respect to playback of the songs from the workout play list.

5. The method of claim 4, wherein the entry in the playlist identification table with the information about the modified playlist comprises information associated with the workout playlist;

wherein the information associated with the workout playlist comprises a workout ID that indicates a workout during which the songs of the workout playlist were played.

6. The method of claim 4, wherein the entry in the playlist identification table with the information about the modified playlist comprises information associated with the workout playlist;

wherein the information associated with the workout playlist is configured to store an identification of user behavior to override the modified playlist.

7. The method of claim 1, further comprising:

in the host computer, performing operations for:

generating and storing a modified playlist as the workout playlist, based upon the physiologic data;

determining that the modified playlist does not correspond to a preexisting playlist prior to suggesting a correlation of the modified playlist with the workout template.

8. The method of claim 1, wherein:

suggesting, to a user, a modification to the workout playlist to correlate to the user behavior comprises:

suggesting the modification relating to a given song in the workout playlist based on the user behavior during at least two instances of playback of the given song during corresponding processing of the workout template.

9. A host computer, comprising:

a processor; and a network interface;

the processor and the network interface performing operations for:

storing a workout playlist of songs for a workout template, the workout template comprising audio cues for a corresponding workout;

processing the workout template, including playing songs in the workout playlist and playing the audio cues during the playing of the songs; and based on physiologic data indicative of user behavior, modifying the audio cues played during the playing of the songs.

10. The host computer of claim 9, comprising generating and storing a modified playlist as the workout playlist, based upon the physiologic data;

wherein storing the modified play list comprises:

updating a corresponding entry in a workout identification table, the entry comprising a workout identification ("ID") and a playlist ID, wherein the workout ID indicates workout characteristics for a workout that corresponds to the workout ID and the playlist ID indicates a playlist that defines media playback associated with the workout;

wherein the updating comprises updating the playlist ID with an identifier for the modified playlist.

11. The host computer of claim 10, wherein the entry in the workout identification table further comprises a template ID, the template ID indicating the audio cues for the corresponding workout.

12. The host computer of claim 9, comprising generating and storing a modified playlist as the workout playlist, based upon the physiologic data;

wherein the generating and storing the modified playlist comprises:

updating a corresponding entry in a playlist identification table with information about the modified playlist, the entry comprising a playlist ID and a listing of media in the workout playlist, wherein the play list ID indicates a designation for the workout playlist;

wherein the updating comprises updating the playlist ID with an identifier for the modified playlist and updating the listing of media in the modified playlist to include media corresponding to the user behavior with respect to playback of the songs from the workout playlist.

13. The host computer of claim 12, wherein the entry in the playlist identification table with the information about the modified playlist comprises information associated with the workout playlist;

wherein the information associated with the workout playlist comprises a workout ID that indicates a workout during which the songs of the workout playlist were played.

14. The host computer of claim 12, wherein the entry in the playlist identification table with the information about the modified playlist comprises information associated with the workout playlist;

wherein the information associated with the workout playlist is configured to store an identification of user behavior to override the modified playlist.

15. The host computer of claim 9, further comprising:

the processor and network interface performing operations for:

generating and storing a modified playlist as the workout playlist, based upon the physiologic data; and determining that the modified playlist does not correspond to a preexisting playlist prior to suggesting a correlation of the modified playlist with the workout template.

16. A non-transitory computer-readable storage medium storing instructions that, when executed by a host computer, cause the host computer to perform a method, the method comprising:

storing a workout play list of songs for a workout template, the workout template comprising audio cues for a corresponding workout;

processing the workout template, including playing songs in the workout playlist and playing the audio cues during the playing of the songs; and based on physiologic data indicative of user behavior, modifying the audio cues played during the playing of the songs.

17. The computer-readable storage medium of claim 16, comprising generating and storing a modified playlist as the workout playlist, based upon the physiologic data;

wherein storing the modified playlist comprises:

updating a corresponding entry in a workout identification table, the entry comprising a workout identification ("ID") and a playlist ID, wherein the workout ID indicates workout characteristics for a workout corresponding to the workout ID and the playlist ID indicates a playlist that defines media playback associated with the workout;

wherein the updating comprises updating the playlist ID with an identifier for the modified playlist.

18. The computer-readable storage medium of claim 17, wherein the entry in the workout identification table further comprises a template ID, the template ID indicating the audio cues for the corresponding workout.

19. The computer-readable storage medium of claim 16, comprising generating and storing a modified playlist as the workout playlist, based upon the physiologic data;

wherein the generating and storing the modified playlist comprises:

updating a corresponding entry in a playlist identification table with information about the modified playlist, the entry comprising a playlist ID and a listing of media in the workout playlist, wherein the playlist ID indicates a designation for the workout playlist;

wherein the updating comprises updating the playlist ID with an identifier for the modified playlist and updating the listing of media in the workout playlist to include media corresponding to the user behavior with respect to playback of the songs from the workout playlist.

20. The computer-readable storage medium of claim 19, wherein the entry in the playlist identification table with the information about the modified playlist comprises information associated with the workout playlist; and wherein the information associated with the workout playlist comprises a workout ID that indicates a workout during which the songs of the workout playlist were played.

* * * * *